United States Patent [19]

Schmitt et al.

[11] Patent Number: 5,169,975
[45] Date of Patent: Dec. 8, 1992

[54] BINARY AZULENESQUARIC ACID DYES, THEIR INTERMEDIATES AND OPTICAL RECORDING MEDIUM

[75] Inventors: Michael Schmitt, Weinheim; Bernhard Albert, Maxdorf; Sibylle Brosius; Klaus D. Schomann, both of Ludwigshafen; Harald Kuppelmaier, Goennheim, all of Fed. Rep. of Germany

[73] Assignee: BASF Aktiengesellschaft, Ludwigshafen, Fed. Rep. of Germany

[21] Appl. No.: 792,916

[22] Filed: Nov. 15, 1991

[30] Foreign Application Priority Data

Dec. 20, 1990 [DE] Fed. Rep. of Germany ....... 4040907

[51] Int. Cl.$^5$ .................... C07C 261/00; C07C 69/76; C07C 233/00; C07C 255/00
[52] U.S. Cl. .................................................... 560/26; 560/51; 560/273; 560/224; 560/225; 564/156; 564/160; 558/303
[58] Field of Search .................. 560/26, 51, 223, 224, 560/285; 564/156, 160; 558/303

[56] References Cited

U.S. PATENT DOCUMENTS

| | | |
|---|---|---|
| 4,990,649 | 2/1991 | Schrott et al. |
| 5,084,592 | 1/1992 | Schrott et al. |
| 5,087,727 | 2/1992 | Schrott et al. |

FOREIGN PATENT DOCUMENTS

| | | |
|---|---|---|
| 0295144 | 12/1988 | European Pat. Off. |
| 0310080 | 4/1989 | European Pat. Off. |
| 0341541 | 11/1989 | European Pat. Off. |
| 0424777 | 5/1991 | European Pat. Off. |
| 0427007 | 5/1991 | European Pat. Off. |

OTHER PUBLICATIONS

Houben-Weyl, "Methoden Der Organischen Chemie", vol. E5, pp. 659–684, 695–700, and 941–964. May 1985.
Houben-Weyl, "Methoden Der Organischen Chemie", vol. E4, pp. 181–189, and 352–364. Jan. 1984.

*Primary Examiner*—Jose G. Dees
*Assistant Examiner*—Keith MacMillan
*Attorney, Agent, or Firm*—Oblon, Spivak, McClelland, Maier & Neustadt

[57] ABSTRACT

Binary azulenesquaric acid dyes of the formula

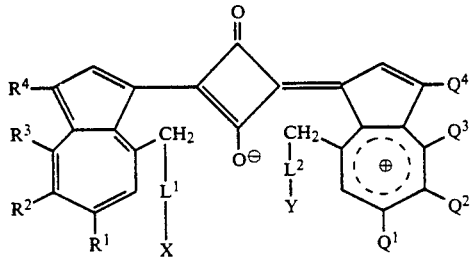

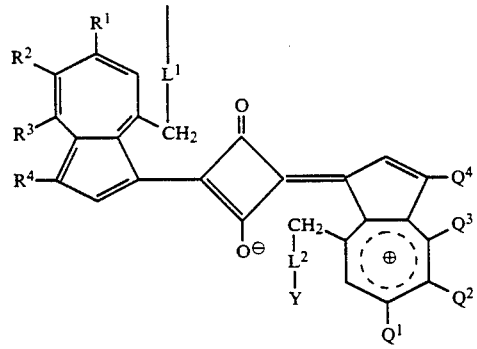

where X is a bridging member, Y is hydrogen, cyano or formula $CO-OR^5$, $CO-NHR^5$, $OR^5$, $O-CO-OR^5$, $NH-CO-R^5$, $NH-CO-OR^5$ or $NH-SO_2-R^5$, where $R^5$ is hydrogen, $C_1$-$C_{12}$-alkyl, $C_2$-$C_{12}$-alkenyl, $C_5$-$C_7$-cycloalkyl or unsubstituted or substituted phenyl, $L^1$ and $L^2$ are each, independently of one another, a chemical bond or unsubstituted or substituted $C_1$-$C_{12}$-alkylene and $R^1$, $R^2$, $R^3$, $R^4$, $Q^1$, $Q^2$, $Q^3$ and $Q^4$ are each, independently of one another, hydrogen or unsubstituted or substituted $C_1$-$C_{12}$-alkyl, their intermediates and an optical recording medium containing the novel dyes are described.

4 Claims, No Drawings

BINARY AZULENESQUARIC ACID DYES, THEIR INTERMEDIATES AND OPTICAL RECORDING MEDIUM

The present invention relates to novel binary azulenesquaric acid dyes of the formula I

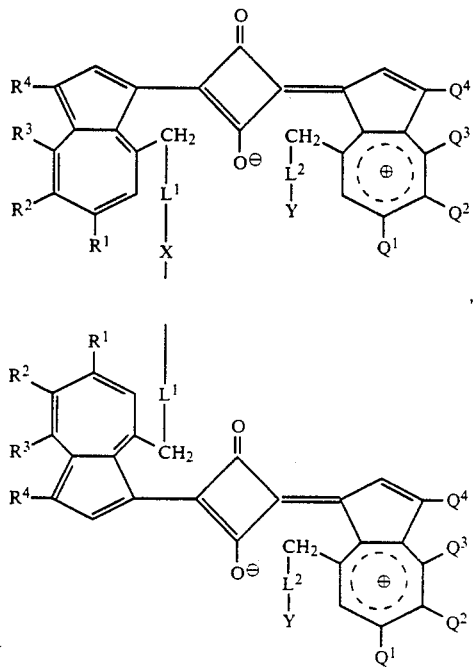

where X is formula CO—O—M—O—CO, CO—NR$^5$—M—NR$^5$—CO, O—CO—M—CO—O or NR$^5$—CO—M—CO—NR$^5$, where R$^5$ is hydrogen, C$_1$-C$_{12}$-alkyl, C$_2$-C$_{12}$-alkenyl, C$_5$-C$_7$-cycloalkyl or substituted or unsubstituted phenyl, and M is C$_1$-C$_{12}$-alkylene, phenylene, biphenylene or formula (C$_2$H$_4$O—)$_n$C$_2$H$_4$ or

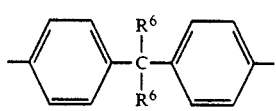

where n is from 1 to 10 and each R$^6$ is hydrogen or C$_1$-C$_4$-alkyl, Y is hydrogen, cyano or formula CO—OR$^5$, CO—NHR$^5$, OR$^5$, O—CO—OR$^5$, NH—CO—R$^5$, NH—CO—OR$^5$ or NH—SO$_2$—R$^5$, where R$^5$ has the abovementioned meaning in each case, L$^1$ and L$^2$ are each, independently of one another, a chemical bond or C$_1$-C$_{12}$-alkylene which is unsubstituted or substituted by phenyl, and R$^1$, R$^2$, R$^3$, R$^4$, Q$^1$, Q$^2$, Q$^3$ and Q$^4$ are each, independently of one another, hydrogen or C$_1$-C$_{12}$-alkyl which can be substituted by halogen, C$_1$-C$_{12}$-alkoxy, unsubstituted or substituted phenyl, C$_1$-C$_{12}$-alkoxycarbonyl or cyano, with the proviso that when R$^4$ and/or Q$^4$ are/is hydrogen the positions of the substituent CH$_2$—L$^1$—X—L$^1$—CH$_2$ and R$^3$ and/or CH$_2$—L$^2$—Y and Q$^3$ on the azulene rings can also be interchanged, to their intermediates and to an optical recording medium containing the novel dyes.

For economic production of optical data recording media there is a need for dyes with special properties. These dyes ought to have

- a strong absorption at 700–900 nm in order to provide semiconductor laser-writable layers
- a high reflectivity in the near infrared (700–900 nm) in the layer in order for a simple layer construction (without reflector layer) to suffice,
- a high solubility in order, for example, to be able to apply the thin storage layer to a substrate by spin-coating and
- high stability in thin layers.

EP-A-310 080 and EP-A-341 541, as well as EP-A-424 777 and EP-A-427 007 have disclosed azulenesquaric acid dyes.

However, many of the storage materials hitherto disclosed often have deficiencies in at least one of the stated requirements.

It is an object of the present invention to provide novel dyes which have the abovementioned deficiencies to only an extremely small extent, if at all.

We have found that this object is achieved by the binary azulenesquaric acid dyes of the formula I defined above.

All the alkyl, alkylene and alkenyl groups occurring in the abovementioned formula I can be either straight-chain or branched.

Suitable substituents for phenyl in formula I are, for example, C$_1$-C$_4$-alkyl, C$_1$-C$_4$-alkoxy or halogen.

Preferred for halogen in each case is fluorine, chlorine or bromine.

Examples of L$^1$ and L$^2$ are methylene, ethylene, 1,2- or 1,3-propylene, 1,2-, 1,3-, 2,3- or 1,4-butylene, pentamethylene, hexamethylene, heptamethylene, octamethylene, nonamethylene, decamethylene or undecamethylene, dodecamethylene, phenylethylene or 1-phenyl-1,3-propylene.

Examples of R$^1$, R$^2$, R$^3$, R$^4$, R$^5$, R$^6$, Q$^1$, Q$^2$, Q$^3$ and Q$^4$ in formula I are methyl, ethyl, propyl, isopropyl, butyl, isobutyl, sec-butyl or tert-butyl.

Further examples of R$^1$, R$^2$, R$^3$, R$^4$, R$^5$, Q$^1$, Q$^2$, Q$^3$ and Q$^4$ are pentyl, isopentyl, neopentyl, tert-pentyl, hexyl, 2-methylpentyl, heptyl, octyl, 2-ethylhexyl, nonyl, decyl, undecyl or dodecyl.

Further examples of R$^5$ are vinyl, allyl, methallyl, ethallyl, cyclopentyl, cyclohexyl, cycloheptyl, 2- or 4-methylphenyl, 2- or 4-methoxyphenyl or 2- or 4-chlorophenyl.

Further examples of R$^1$, R$^2$, R$^3$, R$^4$, Q$^1$, Q$^2$, Q$^3$ and Q$^4$ are fluoromethyl, chloromethyl, difluoromethyl, trifluoromethyl, trichloromethyl, 2-fluoroethyl, 2-chloroethyl, 2-bromoethyl, 1,1,1-trifluoroethyl, heptafluoropropyl, 4-chlorobutyl, 5-fluoropentyl, 6-chlorohexyl, cyanomethyl, 2-cyanoethyl, 3-cyanopropyl, 2-cyanobutyl, 4-cyanobutyl, 5-cyanopentyl, 6-cyanohexyl, 2-methoxyethyl, 2-ethoxyethyl, 2-propoxyethyl, 2-isopropoxyethyl, 2-butoxyethyl, 2-methoxypropyl, 2-ethoxypropyl, 3-ethoxypropyl, 4-ethoxybutyl, 4-isopropoxybutyl, 5-ethoxypentyl, 4-methoxyhexyl, benzyl, 1-phenylethyl, 2-phenylethyl, 4-chlorobenzyl, 4-methoxybenzyl, 2-(4-methylphenyl)ethyl, methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl, 4-ethoxycarbonylbutyl, 5-methoxycarbonylpentyl, 5-ethoxycarbonylpentyl, 6-methoxycarbonylhexyl or 6-ethoxycarbonylhexyl.

Preferred binary azulenesquaric acid dyes of the formula I are those where R$^1$, R$^2$, R$^3$, R$^4$, Q$^1$, Q$^2$, Q$^3$ and Q$^4$ are each hydrogen or C$_1$-C$_6$-alkyl.

Particularly preferred binary azulenesquaric acid dyes of the formula I are those where $R^1$, $R^2$, $R^3$ and $R^4$ are each hydrogen or $C_1-C_6$-alkyl, $Q^1$ and $Q^3$ are each hydrogen, $Q^2$ is isopropyl and $Q^4$ is methyl.

Especially preferred binary azulenesquaric acid dyes of the formula I are those where $R^1$, $R^3$, $Q^1$ and $Q^3$ are each hydrogen, $R^2$ and $Q^2$ are each isopropyl and $R^4$ and $Q^4$ are each methyl.

Particularly important binary azulenesquaric acid dyes of the formula I are those where $L^2$ is a chemical bond and Y is hydrogen.

The novel dyes of the formula I are obtained from binary azulene derivatives of the formula II

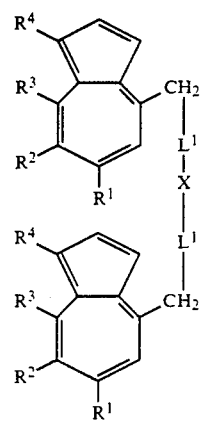

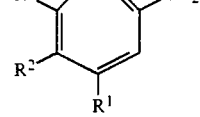

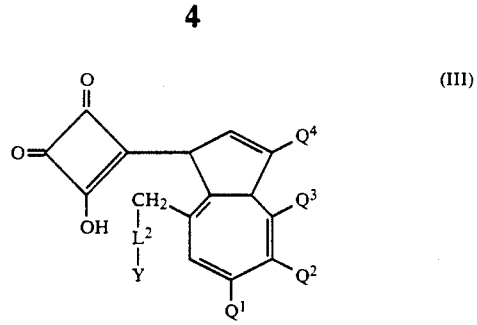

where $L^2$, Y, $Q^1$, $Q^2$, $Q^3$ and $Q^4$ each have the abovementioned meanings, in the molar ratio from 1:2 to 1:3.

Squaric acid derivatives of the formula III are obtained by reacting the azulene derivatives IV with squaryl chloride, where Y, $L^2$, $Q^1$, $Q^2$, $Q^3$ and $Q^4$ each have the abovementioned meanings, as shown by the following equation:

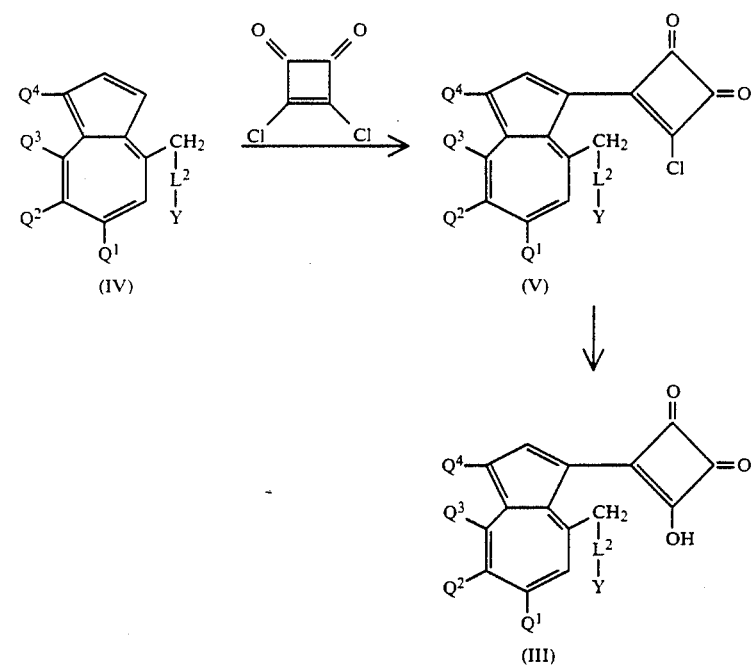

where $L^1$, X, $R^1$, $R^2$, $R^3$ and $R^4$ each have the abovementioned meanings, by reaction with squaric acid derivatives of the formula III In those azulene derivatives of the formulae II and IV where $R^4$ and $Q^4$ are each hydrogen, the squaric acid can be linked to different positions on the five-membered rings, so that isomeric products are possible in which the positions of the substituents $CH_2$—$L^1$—X—$L^1$—$CH_2$ and $R^3$, and $CH_2$—$L^2$—Y and $Q^3$, as indicated above, are interchanged. Thus, a distinction is made between compounds in which the squaric acid is linked on the same side as $CH_2$—$L^1$—X—$L^1$—$CH_2$ or $CH_2$—$L^2$—Y and those in which the squaric acid is linked on the same side as $R^3$ or $Q^3$. The isomers can be separated by chromatography. However, the mixtures of isomers are normally employed in storage layers.

The present invention also relates to novel binary azulene derivatives of the formula II

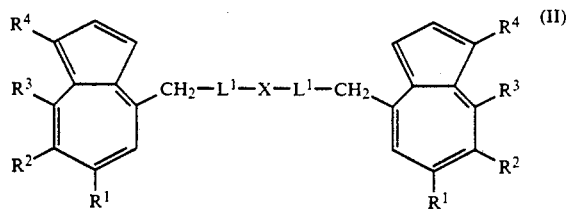 (II)

where X is formula CO—O—M—O—CO, CO—NR$^5$—M—NR$^5$—CO, O—CO—M—CO—O or NR$^5$—CO—M—CO—NR$^5$, where R$^5$ is hydrogen, $C_1$-$C_{12}$-alkyl, $C_2$-$C_{12}$-alkenyl, $C_5$-$C_7$-cycloalkyl or substituted or unsubstituted phenyl, and M is $C_1$-$C_{12}$-alkylene, phenylene, biphenylene or formula (C$_2$H$_4$O—)$_n$C$_2$H$_4$ or

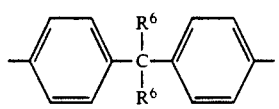

where n is from 1 to 10 and each R$^6$ is hydrogen or $C_1$-$C_4$-alkyl, L$^1$ is a chemical bond or $C_1$-$C_{12}$-alkylene which is unsubstituted or substituted by phenyl, and R$^1$, R$^2$, R$^3$ and R$^4$ are each, independently of one another, hydrogen or $C_1$-$C_{12}$-alkyl which can be substituted by halogen, $C_1$-$C_{12}$-alkoxy, unsubstituted or substituted phenyl, $C_1$-$C_{12}$-alkoxycarbonyl or cyano.

The binary azulene derivatives of the formula II are obtained, for example:
from azulenylalkanecarboxylic acids, which have, for example, the formula VI

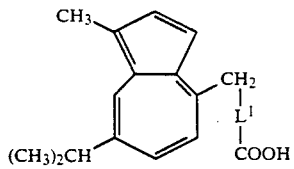 (VI)

where L$^1$ has the abovementioned meanings, and bifunctional hydroxy compounds or bifunctional amines,
from hydroxyalkylazulenes which have, for example, the formula VII

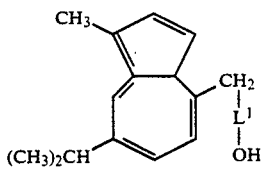 (VII)

where L$^1$ has the abovementioned meanings, and bifunctional acid chlorides,
from azulenylalkylamines which have, for example, the formula VIII

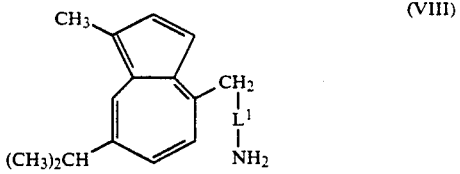 (VIII)

where L$^1$ has the abovementioned meanings, and bifunctional isocyanates or bifunctional acid chlorides.

The said reactions are described, for example, in Houben-Weyl "Methoden der Organischen Chemie" E5, pages 659-684, 695-700, 941-964; E4, pages 181-189 or 352-364.

The azulene derivatives VI, VII and VIII are prepared by conventional methods as described, for example, in EP-A-310 080 or the earlier German Patent Application P 40 39 437.9.

Another object of the present invention was to provide a novel optical recording medium which contains azulenesquaric acid dyes as storage materials, which can be produced in a straightforward manner, whose writability and subsequent readability are both good, which has a high stability of the storage layers and with which the signal/noise ratios should be as high as possible.

The present invention also relates to an optical recording medium containing a substrate and a radiation-sensitive thin coating film containing dye and, possibly, binders, where the dye has the formula I

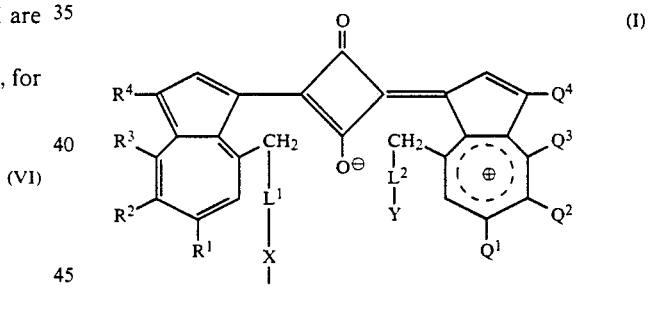 (I)

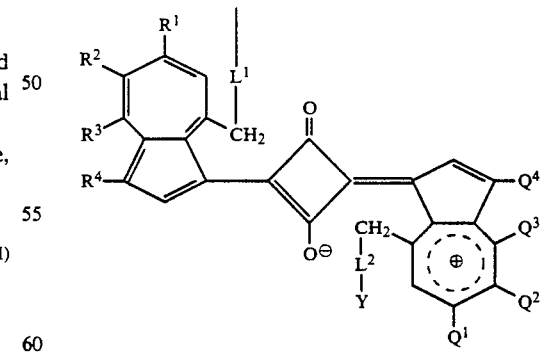

where X is formula CO—O—M—O—CO, CO—NR$^5$—M—NR$^5$—CO, O—CO—M—CO—O or NR$^5$—CO—M—CO—NR$^5$, where R$^5$ is hydrogen, $C_1$-$C_{12}$-alkyl, $C_2$-$C_{12}$-alkenyl, $C_5$-$C_7$-cycloalkyl or substituted or unsubstituted phenyl, and M is $C_1$-$C_{12}$-alkylene, phenylene, biphenylene or formula (C$_2$H$_4$O—)$_n$C$_2$H$_4$ or

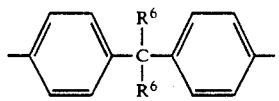

where n is from 1 to 10 and each $R^6$ is hydrogen or $C_1$-$C_4$-alkyl, Y is hydrogen, cyano or formula CO—$OR^5$, CO—$NHR^5$, $OR^5$, O—CO—$OR^5$, NH—CO—$R^5$, NH—CO—$OR^5$ or NH—$SO_2$—$R^5$, where $R^5$ has the abovementioned meaning in each case, $L^1$ and $L^2$ are each, independently of one another, a chemical bond or $C_1$-$C_{12}$-alkylene which is unsubstituted or substituted by phenyl, and $R^1$, $R^2$, $R^3$, $R^4$, $Q^1$, $Q^2$, $Q^3$ and $Q^4$ are each, independently of one another, hydrogen or $C_1$-$C_{12}$-alkyl which can be substituted by halogen, $C_1$-$C_{12}$-alkoxy, unsubstituted or substituted phenyl, $C_1$-$C_{12}$-alkoxycarbonyl or cyano, with the proviso that when $R^4$ and/or $Q^4$ are/is hydrogen the positions of the substituent $CH_2$—$L^1$—X—$L^1$—$CH_2$ and $R^3$ and/or $CH_2$—$L^2$—Y and $Q^3$ on the azulene rings can also be interchanged.

A preferred optical recording medium contains binary azulenesquaric acid dyes of the formula I where $R^1$, $R^2$, $R^3$, $R^4$, $Q^1$, $Q^2$, $Q^3$ and $Q^4$ are each hydrogen or $C_1$-$C_6$-alkyl.

A particularly preferred optical recording medium contains binary azulenesquaric acid dyes of the formula I where $R^1$, $R^2$, $R^3$ and $R^4$ are each hydrogen or $C_1$-$C_6$-alkyl, $Q^1$ and $Q^3$ are each hydrogen, $Q^2$ is isopropyl and $Q^4$ is methyl.

An especially preferred optical recording medium contains binary azulenesquaric acid dyes of the formula I where $R^1$, $R^3$, $Q^1$ and $Q^3$ are each hydrogen, $R^2$ and $Q^2$ are each isopropyl and $R^4$ and $Q^4$ are each methyl.

Suitable substrates are expediently transparent, e.g. made of glass or plastic. Examples of suitable plastics are poly(meth)acrylates, polycarbonates, polyesters, epoxides, polyolefins, e.g. polymethylpentene, polyamide, polyvinyl chloride, polystyrene or polyvinyl esters.

A preferred recording medium has a substrate made of polycarbonate or poly(meth)acrylates, but especially polycarbonate.

Also preferred is an optical recording medium which contains from 1 to 30% by weight, based on dye, of binder.

The novel binary azulenesquaric acid dyes of the formula I have good optical data. In addition, the layers of the pure novel dyes are very stable, i.e. they have an extremely low tendency to crystallize. Thus, to date no recrystallization of the pure dye layer has been observed and hence addition of polymeric binders can be dispensed with. In addition, the fastness to light (stability) is distinctly greater than that of known methine dyes so that addition of stabilizers can be kept to a minimum. It is also particularly advantageous that the novel dyes I are very soluble in most organic solvents so that these dyes can be spincoated directly (without protective layer) on structured plastic substrates, especially polycarbonate substrates.

As mentioned above, the spincoating solution preferably contains a binder in order to ensure good long-term stability of the recording medium and, in particular, to optimize the viscosity of the spincoating solution. The solution preferably contains from 1 to 30% by weight of a binder, based on the dissolved solid content of the spincoating solution. Examples of suitable binders are polyorganosiloxanes, epoxides, poly(meth)acrylates, polystyrene homo- and copolymers, polyvinylcarbazole, polyvinylpyrrolidone, polyimidazole copolymers, polyvinyl ester copolymers, polyvinyl ether copolymers, polyvinylidene chloride copolymers, acrylonitrile copolymers, polyvinyl chloride or copolymers thereof, cellulose acetate or nitrocellulose.

A preferred recording medium contains a binder based on a vinyl pyrrolidone/vinyl acetate copolymer or a polyvinyl chloride/polyvinyl ether copolymer.

The optical recording medium according to the invention is expediently produced by spincoating a solution containing organic solvents and azulenesquaric acid dye I, with or without a binder. It is expedient for the spincoating solution to have a dissolved solid content of from 1 to 30% by weight based on the solution.

Examples of suitable solvents are propanol, isopropanol, butanol, diacetone alcohol, methyl ethyl ketone, toluene, bromoform, 1,1,2-trichloroethane or mixtures thereof.

The solution may also contain 10% by weight, based on the dissolved solid content in the spincoating solution, of additives, e.g. antioxidants, singlet oxygen quenchers or UV absorbers.

The spincoating solution preferably contains up to 5% by weight, based on the dissolved solid content, of a mixture of several antioxidants, singlet oxygen quenchers and UV absorbers. When those antioxidants which likewise absorb in the near infrared are used, for example nickel thiolene complexes, as are described, for example, in DE-A-3,505,750, DE-A-3,05,751 or S. H. Kim, M. Matsuoka, M. Yomoto, Y. Tsuchiva and T. Kitao, Dyes and Pigments, 8 (1987) 381-388, the content is preferably up to 10% by weight of the dissolved solid content in the spincoating solution.

Spincoating means in this connection the application of the solution to the rotating substrate which expediently has a circular shape. However, it is also possible to apply the solution to a substrate while stationary and then to rotate it. Application to the substrate is expediently carried out with a spray or capillaries or using a mechanical pump.

The substrate generally rotates at a speed of from 5 to 7000 rpm, preferably 500 to 5000 rpm, with the spincoating expediently taking place at a lower speed (about 500 to 2000 rpm) and the subsequent drying taking place at a higher speed (about 5000 to 7000 rpm).

The thickness of the layer which is sensitive to laser light is from 40 to 160 nm, preferably 80 to 120 nm. It depends on the speed of rotation, the concentration and the viscosity of the spincoating solution and the temperature.

The layer which is sensitive to laser light on the optical recording medium according to the invention is in the form of a homogeneous, thin, smooth layer which has a high optical quality. Thus, the reflectivity is generally above 12%.

The novel recording medium is, furthermore, sufficiently sensitive at the wavelength of the laser light source used, i.e. on incidence of light pulses with an energy of a few nJ focused to a spot of $\leq 1$ μm there is formation of pits, which results in an excellent signal/-noise ratio.

Particularly suitable laser light sources are, because of the small size of the component, the low energy required and the possibility of direct modulation of the optical output by modulation of the electrical driving current, solid injection lasers which emit in the near infrared, especially the AlGaAs laser which operates in the wavelength range 750-900 nm.

The examples illustrate the invention. I. Preparation of binary azulene derivatives of the formula

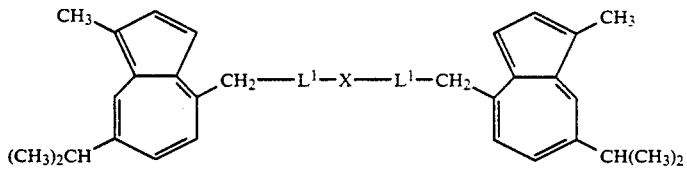

EXAMPLE 1

$L^1$—X—$L^1$:
$C_2H_4$—O—CO—NH—$C_6H_{12}$—NH—CO—O—$C_2H_4$ 21.8 g (0.09 mol) of 7-isopropyl-1-methyl-4-(3-hydroxypropyl)azulene were dissolved in 50 ml of 1,1,1-trichloroethane, and 6.7 g (0.04 mol) of hexamethylene diisocyanate were added. 1 drop of didodecyldibutylstannane was added and the mixture was then refluxed for 2 hours. After the reaction was complete, the solvent was removed under reduced pressure, and the residue was chromatographed on silica gel (acetone/methylene chloride 1:9 v/v).

25 g (96%) of binary azulene derivative were obtained as a dark blue solid of melting point 106°-110° C.

IR (Film): $\bar{v}$=3350 (—NH); 2957, 2932, 2865 (C—H); 1689 (C=O); 1526, 1463, 1438, 1388, 1255 cm$^{-1}$.

$^1$H-NMR (CDCl$_3$): δ=1.2-1.5 (m, 8H); 1.3 (2s, 12H); 2.1 (q, 4H); 2.65 (s, 6H); 3.08 (mc, 2H); 3.15 (m, 8H); 4.15 (t, 4H); 4.7 (bs, 2H; NH); 6.95 (d, 2H); 7.25 (d, 2H); 7.35 (d, 2H), 7.60 (d, 2H), 8.15 (s, 2H) ppm.

$^{13}$C-NMR(CDCl$_3$): δ=12.83 (q, 2C); 24.70 (q, 4C); 26.37 (2C); 30.05 (2C); 30.71 (2C); 34.55 (2C); 38.25 (2C); 41.07 (2C); 64.66 (2C); 112.34 (2C); 124.43 (2C); 125.36 (2C); 133.18 (2C); 135.08 (2C); 136.41 (2C); 136.53 (2C); 137.33 (2C); 139.95 (2C); 147.82 (2C); 156.76 (2C) ppm.

MS (70 eV): m/e=653 (100%, $C_{42}H_{56}N_2O_4^+$).

EXAMPLE 2

$L^1$—X—$L^1$:

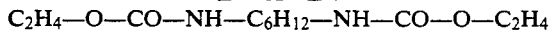

12.1 g (0.05 mol) of 7-isopropyl-1-methyl-4-(3-hydroxypropyl)azulene were dissolved in 50 ml of 1,1,1-trichloroethane, and 5.0 g (0.02 mol) of 4,4'-diisocyanatodiphenylmethane were added. 1 drop of didodecyldibutylstannane was added and the mixture was then refluxed for 2 hours. After the reaction was complete, the solvent was removed under reduced pressure and the residue was chromatographed on silica gel (acetone/methylene chloride 1:40 v/v).

8.4 g (57%) of binary azulene derivative were obtained as a dark blue solid of melting point 144°-145° C.

IR (KBr): $\bar{v}$=3440, 3660 (NH); 2957 (C—H); 1726, 1700 (C=O); 1600, 1521, 1412, 1309, 1227, 1204 cm$^{-1}$.

EXAMPLE 3

$L^1$—X—$L^1$: $C_2H_4$—O—CO—$C_4H_8$—CO—O—$C_2H_4$ 12.1 g (0.05 mol) of 7-isopropyl-1-methyl-4-(3-hydroxypropyl)azulene were dissolved in 70 ml of dichloromethane. 7.9 g (0.1 mol) of pyridine were added and then, at room temperature, a solution of 4.6 g (0.025 mol) of adipyl chloride in 20 ml of dichloromethane was added dropwise. After the reaction was complete, the mixture was hydrolyzed with 200 ml of water and acidified with 2N hydrochloric acid. The organic phase was separated off and dried over sodium sulfate. The solvent was removed under reduced pressure and then the residue was chromatographed on silica gel (petroleum ether/ethyl acetate 9:1 v/v).

12.2 g (41%) of binary azulene derivative were obtained as a dark blue oil. Physical data:

IR (Film): $\bar{v}$=2958, 2868 (C—H); 1734 (C=O); 1462, 1388 cm$^{-1}$.

EXAMPLE 4

$L^1$—X—$L^1$:
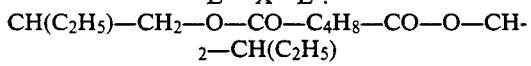

13.5 g (0.05 mol) of 3-(7-isopropyl-1-methyl-4-azulenyl)-2-ethylpropanol were reacted with adipyl chloride and worked up as in Example 3.

13.6 g (33%) of binary azulene derivative were obtained as a dark blue oil. Physical data:

IR (Film): $\bar{v}$=2959, 2932, 2872 (C—H); 1735 (C=O); 1461, 1388 cm$^{-1}$.

EXAMPLE 5

$L^1$—X—$L^1$: $CH_2$—CO—O—$C_2H_4$—O—CO—$CH_2$ 11.8 g (0.06 mol) of dicyclohexylcarbodiimide dissolved in 10 ml of dichloromethane were added dropwise at 0° C. to a solution of 12.8 g (0.05 mol) of 3-(7-isopropyl-1-methyl-4-azulenyl)propionic acid and 1.6 g (0.025 mol) of ethylene glycol in 100 ml of dichloromethane. 0.5 g of 4-(N,N-dimethylamino)pyridine was added and the mixture was then stirred at 0° C. for 4 hours. The precipitate (dicyclohexylurea) was filtered off and the filtrate was washed several times with 2N hydrochloric acid and then dried over sodium sulfate. The residue remaining after removal of the solvent was chromatographed on silica gel (petroleum ether/ethyl acetate 7:3 v/v).

9.8 g (73%) of binary azulene derivative were obtained as a deep blue oil. Physical data:

IR (Film): $\bar{v}$=2957, 2925 (C—H); 1738 (C=O); 1555, 1461, 1387, 1291, 1150 cm$^{-1}$.

EXAMPLE 6

$L^1$—X—$L^1$:
$CH_2$—CO—O—$C_2H_4$—O—$C_2H_4$—O—CO—$CH_2$ 12.8 g (0.05 mol) of 3-(7-isopropyl-1-methyl-4-azulenyl)propionic acid and 2.5 g of diethylene glycol were reacted and worked up as in Example 5.

11.4 g (78%) of binary azulene derivative were obtained as a deep blue oil. Physical data:

IR (Film): $\bar{v}$=2958, 2927 (C—H); 1735 (C=O); 1461, 1387, 1293, 1258, 1177, 1136 cm$^{-1}$.

EXAMPLE 7

$L^1-X-L^1$:
$CH_2-CO-O-C_2H_4-O-C_2H_4-O-C_2H_4-O-CO-CH_2$ 12.8 g (0.05 mol) of 3-(7-isopropyl-1-methyl-4-azulenyl)propionic acid and 3.5 g of triethylene glycol were reacted and worked up as in Example 5.

11.2 g (72%) of binary azulene derivative were obtained as a deep blue oil. Physical data:

IR (Film): $\bar{\nu}=2957, 2926, 2867$ (C—H); 1734 (C=O); 1461, 1387, 1293, 1177, 1145 cm$^{-1}$.

EXAMPLE 8

$L^1-X-L^1$:

$CH_2-CO-O-\langle\bigcirc\rangle-C(CH_3)_2-\langle\bigcirc\rangle-O-CO-CH_2$ 12.8 g (0.05 mol) of 3-(7-isopropyl-1-methyl-4-azulenyl)propionic acid and 5.7 g (0.025 mol) of 2,2-bis(4-hydroxyphenyl)propane were reacted and worked up as in Example 5.

12.8 g (73%) of binary azulene derivative were obtained as a deep blue oil. Physical data:

IR (Film): $\bar{\nu}=2958, 2929$ (C—H); 1758 (C=O); 1196, 1163, 1135 cm$^{-1}$.

EXAMPLE 9

$L^1-X-L^1$:
$C_3H_6-NH-CO-C_6H_{12}-CO-NH-C_3H_6$ 12.75 g (0.05 mol) of 4-(7-isopropyl-1-methyl-4-azulenyl)butylamine were dissolved in 100 ml of dichloromethane, and 7.9 g (0.1 mol) of pyridine were added. To this was slowly added dropwise a solution of 5.3 g (0.025 mol) of hexane-1,6-dicarbonyl chloride in 10 ml of dichloromethane, and the mixture was stirred at room temperature for 2 hours, after which it was hydrolyzed with 200 g of ice-water and acidified with 2N hydrochloric acid. The organic phase was separated off and dried over sodium sulfate, and the residue remaining after removal of the solvent was chromatographed on silica gel.

15 g (91%) of binary azulene derivative were obtained as a deep blue oil. Physical data:

IR (Film): $\bar{\nu}=3300$ (N-H); 1642, 1554 (—CO—NH—); 1463; 1387 cm$^{-1}$.

II. Preparation of binary azulenesquaric acid dyes

EXAMPLE 10 a) 59.5 g (0.3 mol) of guaiazulene dissolved in 100 ml of tetrahydrofuran were slowly added dropwise at room temperature to a solution of 45 g (0.3 mol) of squaryl chloride in 250 ml of tetrahydrofuran. After the reaction was complete, the solution was concentrated and the residue was taken up in 200 ml of hot ethyl acetate. Petroleum ether (boiling point 40°-70° C.) was added until crystallization started. After cooling, the precipitate was filtered off with suction and washed with petroleum ether. 73 g (78%) of 3-chloro-4-(7-isopropyl-1,4-dimethyl-3-azulenyl)cyclobut-3-ene-1,2-dione were obtained as dark brown crystals of melting point 138°-139° C. Physical data:

IR (KBr): 3960, 3840 (C—H); 1790, 1776, 1756 (C=O); 1531, 1508, 1396, 1366, 1229, 1049 cm$^{-1}$.

$^1$H-NMR (CDCl$_3$): $\delta=1.40$ (2s, 6H), 2.58 (s, 3H) 2.92 (s, 3H), 3.18 (m, 1H), 7.45 (d, 1H), 7.65 (d, 1H), 8.05 (s, 1H), 8.26 (s, 1H) ppm.

$^{13}$C-NMR (CDCl$_3$): $\delta=12.76, 24.38$ (2C), 27.43, 38.27, 112.29, 127.90, 133.52, 134.78, 137.41, 137.65, 140.25, 143.93, 148.34, 149.60, 173.43, 188.28, 190.74, 195.93 ppm.

MS: m/e=312.5 ($C_{19}H_{17}ClO_2^+$).

62.4 g (0.2 mol) of 3-chloro-4-(7-isopropyl-1,4-dimethyl-3-azulenyl)cyclobut-3-ene-1,2-dione were refluxed in 200 ml of dioxane, 40 ml of water and 2 ml of concentrated hydrochloric acid for 8 hours. The solvent was removed under reduced pressure, and the remaining oily residue was crystallized by adding dichloromethane. 36.5 g (62%) of 3-hydroxy-4-(7-isopropyl-1,4-dimethyl-3-azulenyl)cyclobut-3-ene-1,2-dione were obtained as dark brown crystals of melting point 120°-123° C. The substance was used without further purification for synthesizing dyes.

b) The compound of the formula was obtained in a similar manner. Melting point >240° C. (decomp.)

c) A mixture of 6.52 g (0.01 mol) of binary azulene derivative from Example 1, 8.0 g (0.027 mol) of 3-hydroxy-4-(7-isopropyl-1,4-dimethyl-3-azulenyl)cyclobut-3-ene-1,2-dione, 40 ml of toluene and 40 ml of n-butanol was refluxed with a water trap for 4 hours. The solvent was removed under reduced pressure and the residue was chromatographed on silica gel (methylene chloride/ethanol 9:1 v/v).

3.6 g (30%) of the binary squaric acid dye of the formula

-continued

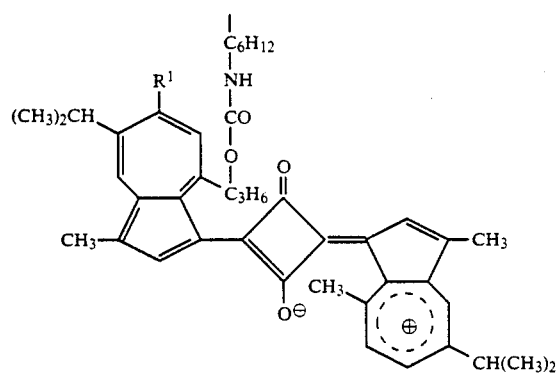

-continued

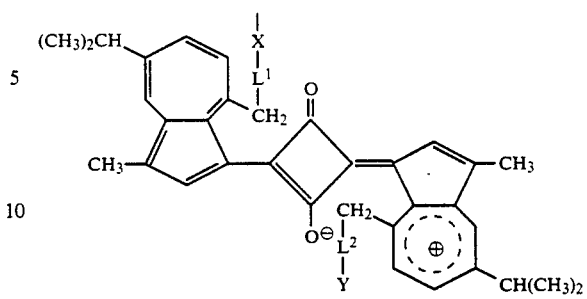

listed in the following table were synthesized in a similar manner to Example 10.

TABLE

| Example No. | $L^1$—X—$L^1$ | $L^2$—Y | $\lambda_{max}$ [nm] $\epsilon$ in $CH_2Cl_2$ | Schm. [°C.] |
|---|---|---|---|---|
| 11 | $C_2H_4$—O—CO—NH—$C_6H_{12}$—NH—CO—O—$C_2H_4$ | $CH(CH_3)$—$CH_2$—O—CO—NH—$C(CH_3)_3$ | 769 (170 000) | 136–141 |
| 12 | $C_2H_4$—O—CO—NH—⟨⟩—$CH_2$—⟨⟩—NH—CO—O—$C_2H_4$ | H | 772 (204 000) | 155–156 |
| 13 | $C_2H_4$—O—CO—$C_4H_8$—CO—O—$C_2H_4$ | H | 769 (195 000) | 110–120 |
| 14 | $CH(C_2H_5)$—$CH_2$—O—CO—$C_4H_8$—CO—O—$CH_2$—$CH(C_2H_5)$ | H | 770 (195 000) | 221–223 |
| 15 | $CH_2$—CO—O—$C_2H_4$—O—CO—$CH_2$ | H | 765 (185 000) | 93–94 |
| 16 | $CH_2$—CO—($OC_2H_4$—$)_2$O—CO—$CH_2$ | H | 764 (210 000) | 120–127 |
| 17 | $CH_2$—CO—($OC_2H_4$—$)_3$O—CO—$CH_2$ | H | 764 (215 000) | 107–109 |
| 18 | $CH_2$—CO—O—⟨⟩—$C(CH_3)_2$—⟨⟩—O—CO—$CH_2$ | H | 761 (220 000) | 102–103 |
| 19 | $C_3H_6$—NH—CO—$C_6H_{12}$—CO—NH—$C_3H_6$ | H | 765 (170 000) | 136–145 | were obtained as a deep blue oil which crystallized on trituration with ethyl acetate/petroleum ether as a bluish green solid of melting point 131°–136° C. Physical data:

IR (KBr): $\bar{v}$=2960, 2930, 2870 (C—H); 1714 (C=O); 1610, 1540, 1431, 1385, 1337, 1249, 1010 $cm^{-1}$. UV ($CH_2Cl_2$): $\lambda_{max}(\epsilon)$=769 (180 000) nm.

The squaric acid dyes of the formula

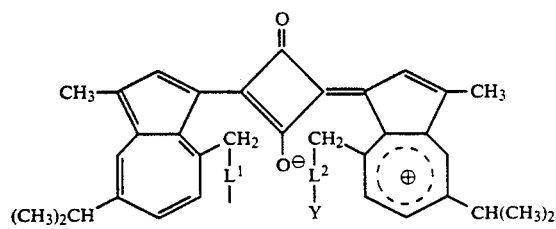

EXAMPLE 20

A 5% by weight solution of the dye from Example 10 in toluene was applied with a spray to a poly(methyl methacrylate) disk rotating at 2000 rpm, and then the remaining solvent was removed at 5000 rpm. The result was a homogeneous, highly reflective dye layer whose writability with a semiconductor laser ($\lambda$=830 nm) was very good. The information can be read out again with good contrast.

EXAMPLE 21

A 3% by weight solution of the dye from Example 10, which contains 30% by weight, based on the dissolved solid content of the solution, of poly(methyl methacrylate), was spincoated onto a grooved polycarbonate disk as in Example 20. The result was a homogeneous, highly reflective dye layer which adheres well to the substrate, images the tracking grooves of the substrate well and whose writability with a semiconductor laser ($\lambda$=830 nm) was very good. The information written in was stable to heat and humidity and can be read out again as often as wanted with good contrast.

EXAMPLE 22

A 2% by weight solution of the dye from Example 10 in propanol/diacetone alcohol (1:1 v/v), which contained 10% by weight of a phenol resin as binder and 5% by weight of 4-octyl-4'-fluorodiphenyldithiolene nickel as stabilizer, based on the dissolved solid content of the solution, was spincoated onto a grooved polycarbonate disk as in Example 20. The resulting storage layer was comparable in every respect to that from Example 20, but had greater stability to UV light.

EXAMPLE 23

A 2% by weight solution of the dye from Example 10 in toluene, which contained 10% by weight of poly(methyl methacylate) and 5% by weight of biscamphoratodithiolenenickel, based on the dissolved solid content of the solution, was spincoated onto a glass disk as in Example 20. The resulting dye layer was homogeneous and had a high basic reflectivity. Its writability with a semiconductor laser ($\lambda = 780$ nm) was good. The information written in is stable under the usual test conditions and can be read out again as often as wanted.

We claim:

1. A binary azulenesquaric acid dye of the formula I

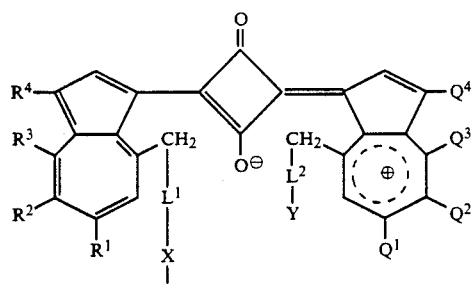

(I)

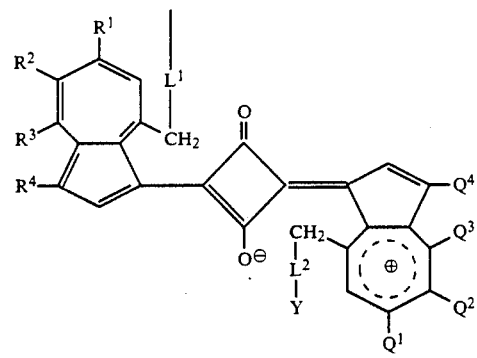

where X is formula CO—O—M—O—CO, —O—CO—NR$^5$—M—NR$^5$—COO, CO—NR$^5$—M—NR$^5$—CO, O—CO—M—CO—O or NR$^5$—CO—M—CO—NR$^5$, where R$^5$ is hydrogen, C$_1$-C$_{12}$-alkyl, C$_2$-C$_{12}$-alkenyl, C$_5$-C$_7$-cycloalkyl or substituted or unsubstituted phenyl, and M is C$_1$-C$_{12}$-alkylene, phenylene, biphenylene or formula (C$_2$H$_4$O—)$_n$C$_2$H$_4$ or

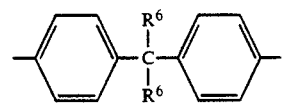

where n is from 1 to 10 and each R$^6$ is hydrogen or C$_1$-C$_4$-alkyl, Y is hydrogen, cyano or formula CO—OR$^5$, CO—NHR$^5$, OR$^5$, O—CO—OR$^5$, NH—CO—R$^5$, NH—CO—OR$^5$ or NH—SO$_2$—R$^5$, where R$^5$ has the abovementioned meaning in each case, L$^1$ and L$^2$ are each, independently of one another, a chemical bond or C$_1$-C$_{12}$-alkylene which is unsubstituted or substituted by phenyl, and R$^1$, R$^2$, R$^3$, R$^4$, Q$^1$, Q$^2$, Q$^3$ and Q$^4$ are each, independently of one another, hydrogen or C$_1$-C$_{12}$-alkyl which can be substituted by halogen, C$_1$-C$_{12}$-alkoxy, unsubstituted or substituted phenyl, C$_1$-C$_{12}$-alkoxycarbonyl or cyano, with the proviso that when R$^4$ and/or Q$^4$ are/is hydrogen the positions of the substituent CH$_2$—L$^1$—X—L$^1$—CH$_2$ and R$^3$ and/or CH$_2$—L$^2$—Y and Q$^3$ on the azulene rings can also be interchanged.

2. A binary azulenesquaric acid dye as claimed in claim 1, wherein R$^1$, R$^2$, R$^3$, R$^4$, Q$^1$, Q$^2$, Q$^3$ and Q$^4$ are each hydrogen or C$_1$-C$_6$-alkyl.

3. A binary azulenesquaric acid dye as claimed in claim 1, wherein R$^1$, R$^2$, R$^3$ and R$^4$ are each hydrogen or C$_1$-C$_6$-alkyl, Q$^1$ and Q$^3$ are each hydrogen, Q$^2$ is isopropyl and Q$^4$ is methyl.

4. A binary azulenesquaric acid dye as claimed in claim 1, wherein R$^1$, R$^3$, Q$^1$ and Q$^3$ are each hydrogen, R$^2$ and Q$^2$ are each isopropyl and R$^4$ and Q$^4$ are each methyl.

* * * * *